US010308676B2

(12) United States Patent
Tilstam et al.

(10) Patent No.: US 10,308,676 B2
(45) Date of Patent: Jun. 4, 2019

(54) METHODS OF MAKING ONAPRISTONE INTERMEDIATES

(71) Applicant: CONTEXT BIOPHARMA INC., Philadelphia, PA (US)

(72) Inventors: Ulf Tilstam, Hoegaarden (BE); Stefan Proniuk, Austin, TX (US); Holger Bindernagel, Gelnhausen (DE); Silvia Werner, Kahl (DE); Holger Rauter, Flieden (DE)

(73) Assignee: CONTEXT BIOPHARMA INC., Philadelphia, PA (US)

( * ) Notice: Subject to any disclaimer, the term of this patent is extended or adjusted under 35 U.S.C. 154(b) by 0 days.

(21) Appl. No.: 15/274,555

(22) Filed: Sep. 23, 2016

(65) Prior Publication Data

US 2017/0088579 A1    Mar. 30, 2017

Related U.S. Application Data

(60) Provisional application No. 62/233,166, filed on Sep. 25, 2015.

(51) Int. Cl.
*C07J 33/00* (2006.01)
*C07J 41/00* (2006.01)

(52) U.S. Cl.
CPC ......... *C07J 33/005* (2013.01); *C07J 41/0083* (2013.01)

(58) Field of Classification Search
CPC .................................................... C07J 33/005
See application file for complete search history.

(56) References Cited

U.S. PATENT DOCUMENTS

| | | |
|---|---|---|
| 4,742,000 A | 5/1988 | Greene |
| 4,774,236 A | 9/1988 | Cook et al. |
| 4,780,461 A | 10/1988 | Neef et al. |
| 4,843,157 A | 6/1989 | Neef et al. |
| 5,141,961 A | 8/1992 | Coapman |
| 5,273,971 A | 12/1993 | Scholz et al. |
| 5,283,190 A | 2/1994 | Traish et al. |
| 5,446,036 A | 8/1995 | Scholz et al. |
| 5,693,628 A | 12/1997 | Schubert et al. |
| 6,093,707 A | 7/2000 | Cook et al. |
| 6,143,754 A | 11/2000 | Chwalisz et al. |
| 6,537,584 B1 | 3/2003 | Zentner et al. |
| 6,750,015 B2 | 6/2004 | Horwitz et al. |
| 6,900,193 B1 | 5/2005 | Kim et al. |
| 7,078,781 B2 | 7/2006 | Hatakeyama et al. |
| 7,678,781 B2 | 3/2010 | Fiordeliso et al. |
| 8,121,365 B2 | 2/2012 | Pinard et al. |
| 8,709,463 B2 | 4/2014 | Looney et al. |
| 9,046,534 B2 | 6/2015 | Gilles |
| 9,193,757 B2 | 11/2015 | Proniuk |
| 9,328,346 B2 | 5/2016 | Lee et al. |
| 9,618,512 B2 | 4/2017 | Endou et al. |
| 2003/0099641 A1 | 5/2003 | Smith et al. |
| 2004/0072811 A1 | 4/2004 | Hoffmann et al. |
| 2004/0121304 A1 | 6/2004 | Fuhmann et al. |
| 2006/0063190 A1 | 3/2006 | Fischer et al. |
| 2006/0111577 A1 | 5/2006 | Kim et al. |
| 2007/0166372 A1 | 7/2007 | Huang et al. |
| 2007/0166753 A1 | 7/2007 | Mass |
| 2007/0167971 A1 | 7/2007 | Huey et al. |
| 2008/0200440 A1 | 8/2008 | Fuhrmann et al. |
| 2011/0003753 A1 | 1/2011 | Waxman |
| 2011/0053900 A1 | 3/2011 | Podolski et al. |
| 2011/0293511 A1 | 12/2011 | Johns et al. |
| 2012/0010790 A1 | 1/2012 | Kanayama et al. |
| 2012/0140790 A1 | 6/2012 | Ali et al. |
| 2012/0230983 A1 | 9/2012 | Muller et al. |
| 2013/0018027 A1 | 1/2013 | Podolski et al. |
| 2013/0029953 A1 | 1/2013 | Nickisch et al. |
| 2013/0095170 A1 | 4/2013 | Gilles |
| 2013/0316992 A1 | 11/2013 | Lange et al. |
| 2013/0338016 A1 | 12/2013 | McDonough et al. |
| 2014/0271819 A1 | 8/2014 | Proniuk |
| 2014/0363425 A1 | 12/2014 | Graham et al. |
| 2015/0241432 A1 | 8/2015 | Berois et al. |
| 2015/0241435 A1 | 8/2015 | Gilles |
| 2015/0285803 A1 | 10/2015 | Gilles et al. |
| 2016/0166583 A1 | 6/2016 | Zukiwski et al. |
| 2017/0088579 A1 | 3/2017 | Tilstam et al. |
| 2017/0182065 A1 | 6/2017 | Brittain et al. |
| 2017/0266204 A1 | 9/2017 | Proniuk et al. |

FOREIGN PATENT DOCUMENTS

| | | |
|---|---|---|
| CN | 1087090 | 11/1992 |
| DE | 3321826 A1 | 12/1984 |
| EP | 0129499 A2 | 12/1984 |
| EP | 0447014 A2 | 9/1991 |

(Continued)

OTHER PUBLICATIONS

Guohua, C., et al. "Synthesis of Progesterone Receptor Antagonist ZK98299." J. of China Pharmaceutical University. (1992), vol. 23, Issue 4, pp. 209-212. (Year: 1992).*

International Search Report and Written Opinion of PCT Application No. PCT/US2016/053435 dated Dec. 15, 2016.

Klijn et al., Progesterone antagonists and progesterone receptor modulation in the treatment of breast cancer, Steroids, v. 65, pp. 825-830 (2000).

Jonat et al., The clinical efficacy of progesterone antagonists in breast cancer, Endocrine Therapy of Breast Cancer, pp. 117-124.

Neef, G. et al, New steroids with antiprogestational and antiglucocorticoid activities, Steroids, 1984, vol. 44, No. 4, p. 349-372.

(Continued)

*Primary Examiner* — Noble E Jarrell
*Assistant Examiner* — John S Kenyon
(74) *Attorney, Agent, or Firm* — Pepper Hamilton LLP

(57) ABSTRACT

Methods and systems for making intermediates in the synthesis of onapristone are provided. Aspects include the photoconversion of onapristone synthesis intermediates using a narrow band frequency light source.

14 Claims, 1 Drawing Sheet

(56) References Cited

FOREIGN PATENT DOCUMENTS

| EP | 0803250 | A1 | 10/1997 | |
|---|---|---|---|---|
| JP | H07509218 | A | 10/1995 | |
| JP | 2011511011 | A | 4/2011 | |
| JP | 2012533539 | | 12/2012 | |
| WO | 1998/031702 | A1 | 7/1998 | |
| WO | 2002072813 | A1 | 9/2002 | |
| WO | 2006010097 | A2 | 1/2006 | |
| WO | 2006111856 | A1 | 10/2006 | |
| WO | 2007/078599 | A2 | 7/2007 | |
| WO | 2008128783 | A2 | 10/2008 | |
| WO | 2009/134725 | A2 | 11/2009 | |
| WO | 2012/087983 | A1 | 6/2012 | |
| WO | 2012083017 | A2 | 6/2012 | |
| WO | 2012122514 | A1 | 9/2012 | |
| WO | 2013/016725 | A1 | 1/2013 | |
| WO | 2013/052652 | A1 | 4/2013 | |
| WO | 2013/086379 | A2 | 6/2013 | |
| WO | 2014093918 | A1 | 6/2014 | |
| WO | 2014/197653 | A2 | 12/2014 | |
| WO | WO-2016154203 | A1 * | 9/2016 | ............ C07J 1/0096 |

OTHER PUBLICATIONS

Chen, G. et al. Zhogguo Yaoke Daxue Xuebao, 1992, 23, 20.
Kojima, Takashi, To improve efficiency of selecting crystal shape with drug development, Journal of Pharmaceutical Science and Technology, Japan, Sep. 1, 2008, vol. 68, No. 5, p. 344-349.
Kawaguchi, Yoko et al, Drug and crystal polymorphism, Journal of Human Environmental Engineering, 2002, Voo.4, No. 2, p. 310-7.
May 1, 2001, PMSB/ELD Notification No. 568. Test Procedures and Acceptance Criteria for New Drug Substances and New Drug Products from Pharmaceutical Evaluation Division of Ministry of Health, Labour and Welfare.
Ajiazawa, Kazuhide, Polym01phism of drugs and science of crystallization, 2002, p. 273, 278, 305-317.
Hirayama, Noriaki, Handbook for producing organic compound crystal, 2008, p. 17-23, 37-40, 45-51, 57-65.
Hancock, B. C., et al, Journal of Pharmaceutical Sciences, 1997, vol. 86, No. I, pp. 1-12.
Yamano, Mitsuhisa, Approach to Crystal Polymorph in Process Research of New Drug, Journal of Synthetic Organic Chemistry, Japan, Sep. 2007, vol. 65, No. 9, p. 907(69)-913(75).
Bamberger et al: "Progesterone receptor isoforms, PR-Band PR-A, in breast cancer: Correlations with clinico pathologic tumor parameters and expression of AP-1 factors", Hormone Research 2000 CH, vol. 54, No. 1, 2000.
Ariga Naohiro et al: "Progesterone receptor A and B isoforms in the human breast and its disorders", Japanese Journal of Cancer Research, vol. 92, No. 3, Mar. 2001.
T. A. Hopp et al: "Breast Cancer Patients with Progesterone Receptor PR-A-Rich Tumors Have Poorer Disease-Free Survival Rates", Clinical Cancer Research, vol. 10, No. 8, Apr. 15, 2004.
Mote PA et al: "Progesterone Receptor Isoforms in Normal and Malignant Breast", Progestins and the Mammary Gland, Springer Berlin Heidelberg, Berlin, Heidelberg, vol. 2007/1, Jan. 1, 2008.
Bonneterre et al: "Abstract PS-02-13: Triple negative breast cancer, the impact of isotype-specific progesterone receptor antibodies on the diagnosis results Cancer Research". May 1, 2015.
Arnett-Mansfield, et al., "Subnuclear Distribution of Progesterone Receptors A and B in Normal and Malignant Endometrium", J Clin Endocrinol Metab, Mar. 2004, vol. 89, No. 3, pp. 1429-1442.
Arnett-Mansfield, et al., "Focal Subnuclear Distribution of Progesterone Receptor is Ligand Dependent and Associated with Transcriptional Activity," Mol Endocrinol, Jan. 2007, vol. 2, No. 1, pp. 14-29.
Etreby, et al., "Antitumor Activity of Mifepristone in the Human LNCaP, LNCaP—C4, and LNCaP—C4—2 Prostate Cancer Models in Nude Mice", The Prostate, 2000, vol. 42, No. 2, pp. 99-106.

Grunberg et al., "Long-Term Administration of Mifepristone (RU486): Clinical Tolerance During Extended Treatment of Meningioma", Cancer Investigation, Jun. 11, 2009, 24:8, pp. 727-733.
McGowan et al., "Cytoskeletal Responsiveness to Progestins is Dependent on Progesterone Receptor A Levels," Journal of Molecular Endocrinology, 2003, 31, pp. 241-253.
Mote et al., "Detection of Progesterone Receptor Forms A and B by Immunohistochemical Analysis," Journal of Clinical Pathology, 2001; 54; pp. 624-630.
Thike et al., "Triple-Negative Breast Cancer; Clnicopathological Characteristics and relationship with Basal-Like Breast Cancer," Modern Pathology, 2010; 23; pp. 123-133.
Jang, Graham R. et al; Cytochrome P4503A4-Mediated N-Demethylation of the Antiprogestins Lilopristone and Onapristone; The American Society for Pharmacology and Experimental Therapeutics (1997), pp. 1119-1122; vol. 25, No. 10.
Baillie, Thomas A. et al; Role of Biotransformation in Drug-Induced Toxicity: Influence of Intra- and Inter-Species Differences in Drug Metabolism; Drug Metab Pharmacokinet. 2011 ; 26(1): 15-29.
Yanni;Translational ADMET for Drug Therapy: Principles, Methods, and Pharmaceutical Applications. Wiley ISBN-13: 978-1118838273 (2015), pp. 63-109.
Pearson P, Wienkers L, editors. Handbook of drug metabolism. New York: Informa Healthcare; 2009. pp. 44X 464.
Kamimura H, Nakada N, Suzuki K, et al. Assessment of chimeric mice with humanized liver as a tool for predicting circulating human metabolites. Drug Metab Pharmacokinet 2010;25(3):223 235.
Shi, Roger et al., Antigen Retrieval Immunohistochemistry under the influence of pH using monoclonal antibodies. Journal of Histochemistry and Cytochemistry; Mar. 1995; vol. 43, pp. 193-201.
Zala, Shailesh et al., Laboratory Techniques of Purification and Isolation. Int. J. Drug Dev. & Res., Apr.-Jun. 2012, 4 (2): 41-55.
Bergstrom, Christel et al., Accuracy of calculated pH-dependent aqueous drug solubility. European Journal of Pharmaceutical Sciences 22 (2004) pp. 387-398.
Robertson, JFR et al., Onapristone, a Progesterone Receptor Antagonist, as First-line Therapy in Primary Breast Cancer. European Journal of Cancer, (1999) vol. 35, No. 2, pp. 214-219.
Graham, J. Dinny et al., Characterization of Progesterone Receptor A an dB Expression in Human Breast Cancer. Cancer Research (Nov. 1, 1995) 55, 5063-5068.
Bailey, Timothy L. et al., MEME: discovering and anlyzing DNA and protein sequence motifs, Nucleic Acids Research, (2006) vol. 34, pp. W369-W373.
Bailey et al., The value of position-specific priors in motif discovery using MEME; BMC Bioinformatics; (2010); 11 :179; BioMed Central Ltd; AU.
Ballare et al., Nucleosome-Driven Transcription Factor Binding and Gene Regulation; Molecular Cell; (2013); 49; 1-13; Elsevier Inc.
Belikov et al., FoxA 1 Binding Directs Chromatin Structure and the Functional Response of a Glucocorticoid Receptor-Regulated Promoter; Molecular and Cellular Biology; (Oct. 2009); vol. 29, No. 20; 5413-5425; American Society for Microbiology.
Clarke et al., Monoclonal Antibodies to Human Progesterone Receptor: Characterization by Biochemical and Immunohistochemical Techniques; Endocrinology; (1987); vol. 121, No. 3; The Endocrine Society; USA.
Clarke, Christine et al., Progestin Regulation of Cellular Proliferation, Endrocrine Reviews (1990), vol. 11, No. 2, pp. 266-301; The Endocrine Society; USA.
Garcia-Bassets et al., Histone Methylation-Dependent Mechanisms Impose Ligand Dependency for Gene Activation by Nuclear Receptors; (2007); Cell; 128; 505-518; Elsevier Inc.
Graham et al., Characterization of Progesterone Receptor A and B Expression in Human Breast Cancer; Cancer Research; (Nov. 1995); 55; 5063-5068; American Association for Cancer Research; USA.
Graham et al., Physiological Action of Progesterone in Target Tissues; Endocrine Reviews; (1997); vol. 18, No. 4; 502-519; The Endocrine Society; USA.

(56) References Cited

OTHER PUBLICATIONS

Heinz et al., Simple Combinations of Lineage-Determining Transcriptions Factors Prime cis-Regulatory Elements Required for Macrophage and B Cell Identities; Molecular Cell; (May 2010); 38; 576-589; Elsevier Inc.
Ui et al., An integrated software system for analyzing Ch IP-chip and Ch IP-seq data; Nature Biotechnology; (Nov. 2008); vol. 26, No. 11; 1293-1300; Nature Publishing Group; USA.
John et al., Chromatin accessibility pre-determines glucocorticoid receptor binding patterns; Nature Genetics; (2011 ); Nature America, Inc.; USA.
Metzger et al., LSD1 demethylates repressive histone marks to promote androgen-receptor-dependent transcription; Nature; (2005); vol. 437; 436-439; Nature Publishing Group.
Murtagh et al., The Nuclear Factor I (NFI) Gene Family in Mammary Gland Development and Function; Journal of Mammary Gland Biology and Neoplasia; (Apr. 2003); vol. 8, No. 2; 241-254; Plenum Publishing Corporation.
Clarke et al., Non-Overlapping Progesterone Receptor Cistromes Contribute to Cell-Specific Transcriptional Outcomes; PLoS; (Apr. 2012); vol. 7, Issue 4.
Rayasam et al., Ligand-Specific Dynamics of the Progesterone Receptor in Living Cells and during Chromatin Remodeling In Vitro; Molecular and Cellular Biology; (Mar. 2005); 2406-2418.
Chapman et al., GenePattern 2.0; Nature Genetics; (2006); vol. 38, No. 5; Nature Publishing Group.
Streuli et al., Stat5 as a Target for Regulation by Extracellular Matrix; The Journal of Biological Chemistry; (1995); vol. 270, No. 37; 21639-21644; The American Society for Biochemistry and Molecular Biology, Inc.; USA.
Yin et al., Genome-Wide Progesterone Receptor Binding: Cell Type-Specific and Shared Mechanisms in T47D Breast Cancer Cells and Primary Leiomyoma Cells; PLoS One; (2012); vol. 7, Issue 1.
Ace et al., Microarray profiling of progesterone-regulated endometrial genes during the rhesus monkey secretory phase; Reproductive Biology and Endocrinology; (2004); 2:54; 1-10; BioMed Central; USA.
Beguelin et al., Progesterone Receptor Induces ErbB-2 Nuclear Translocation to Promote Breast Cancer Growlh via a Novel Transcriptional Effect: ErbB-2 Function as a Coactivator of Stat3; Molecular and Cellular Biology; (Dec. 2010); vol. 30, No. 23; 5456-5472; American Society for Microbiology; USA.
Beral et al., Breast cancer and hormone-replacement therapy in the Million Women Study; The Lancet; (Aug. 2003); vol. 362; 419-427.
Beral et al., Breast Cancer Risk in Relation to the Interval Between Menopause and Starting Hormone Therapy; UNCI; (Feb. 2011); vol. 103, Issue 4; 296-305; Oxford University Press; UK.
Bernardo et al., FOXA1 is an essential determinant of ERα expression and mammary ductal morphogenesis; Development 137; (201 O); 2045-2054; The Company of Biologists Ltd.; USA.
Bolton et al., Cell- and gene-specific regulation of primary target genes by the androgen receptor; Genes Dev.; (2007); 21; 2005-2017; Cold Spring Harbor Laboratory Press; USA.
Borthwick et al., Determination of the transcript profile of human endometrium; Molecular Human Reproduction; (2003); vol. 9, No. 1; 19-33; European Society of Human Reproduction and Embryology; UK.
Bravieri et al., Different DNA contact schemes are used by two winged helix proteins to recognize a DNA binding sequence; Nucleic Acids Research; (1997); vol. 25, No. 14; 2888-2896; Oxford University Press; USA.
Carroll et al., Genome-wide analysis of estrogen receptor binding sites; Nature Genetics; (Nov. 2006); vol. 38, No. 11; 1289-1297; Nature Publishing Group; USA.
Chlebowski et al., Estrogen Plus Progestin and Breast Cancer Incidence and Mortality in Postmenopausal Women; JAMA; (2010); vol. 304, No. 15; 1684-1692; American Medical Association; USA.
Cicatiello et al., Estrogens and Progesterone Promote Persistent CCND1 Gene Activation during G by Inducing Transcriptional Derepression via c-Jun/c-Fos/Estrogen Receptor (Progesterone Receptor) Complex Assembly to a Distal Regulatory Element and Recruitment of Cyclin D1 to Its Own Gene Promoter; Molecular and Cellular Biology; (2004); vol. 24, No. 16; 7260-7274; American Society for Microbiology; USA.
Cirillo et al., Specific Interactions of the Wing Domains of FOXA1 Transcription Factor with DNA; J_ Mal. Biol. (2006); 366; 720-724; Elsevier Lid.
Faivre et al., Progesterone Receptor Rapid Signaling Mediates Serine 345 Phosphorylation and Tethering to Specificity Protein 1 Transcription Factors; Molecular Enocrinology; (2008); 22(4) 823-837; The Endocrine Society; USA.
Friedman et al., The Foxa family of transcription factors in development and metabolism; Cell. Mol. Life. Sci.; (2006); vol. 63; 2317-2328.
Graham et al., Altered Progesterone Receptor Isoform Expression Remodels Progestin Responsiveness of Breast Cancer Cells; Molecular Endocrinology; (Nov. 2005); 19(11); 2713-2735; The Endocrine Society; USA.
Graham et al., DNA Replication Licensing and Progenitor Numbers Are Increased by Progesterone in Normal Human Breast; Endocrinology; (2009); 150(7); 3318-3326; The Endocrine Society; USA.
Hubler et al., Intronic hormone response elements mediate regulation of FKBP5 by progestins and glucocorticoids; Cell Stress & Chaperones; (2004) 09 (3), 243-252; Cell Stress Society International 2004; USA.
Hurtado et al., FOXA 1 is a key determinant of estrogen receptor function and endocrine response; Nature Genetics; (Jan. 2011 ); vol. 43, No. 1; 27-43; Nature America, Inc.; USA.
Joseph et al., Integrative model of genomic factors for determining binding site selection by estrogen receptor-a; Molecular Systems Biology 6; (2010); Article No. 456; Macmillan Publishers Limited.
Kao et al.,Global Gene Profiling in Human Endometrium during the Window of Implantation; Endocrinology; (2002); 143(6); 2119-2138; The Endocrine Society; USA.
Krum et al., Unique ERα Cistromes Control Cell Type-Specific Gene Regulation; Molecular Endocrinology; (2008); 22 (11 ); 2393-2406; The Endocrine Society; USA.
Kushner et al., Estrogen receptor pathways to AP-1; Journal of Steroid Biochemistry & Molecular Biology; (2000); vol. 74; 311-317; Pergamon.
Langmead et al., Ultrafast and memory-effiicient alignment of short DNA sequences to the human genome; Genome Biology; (2009); vol. 10, Issue 3, Article R25; Biomed Central Lid.; USA.
Lieberman et al., The Constitution of a Progesterone Response Element; Molecular Endocrinology; (1993); vol. 7, No. 4; 515-527; The Endocrine Society, Denver; USA.
Liu et al., Sequential recruitment of steroid receptor coactivator-1 (SRC-1) and p300 enhances progesterone receptor-dependent initiation and reinitiation of transcription from chromatin; PNAS; (Sep. 7, 2001 ); vol. 98, No. 22; 12426-12431; Houston, USA.
Longacre et al., A Correlative Morphologic Study of Human Breast and Endometrium in the Menstrual Cycle; The American Journal of Surgical Pathology; (1986); vol. 10, No. 6; Raven Press; New York.
Lupien et al., FoxA 1 Translates Epigenetic Signatures into Enhancer-Driven Lineage-Specific Transcription; Cell; (Mar. 2008); vol. 132; 958-970; Elsevier Inc.
Macquarrie et al., Genome-wide transcription factor binding: beyond direct target regulation; Trends in Genetics; (2011 ); Cell Press.
McKenna et al., Combinatorial Control of Gene Expression by Nuclear Receptors and Coregulators; Cell; (Feb. 22, 2002); vol. 108; 465-474; Cell Press; Houston, USA.
Mortazavi et al., Mapping and quantifying mammalian transcriptomes by RNA-Seq; Nature Methods; (Jul. 2008); vol. 5, No. 7; 621-628; Nature Publishing Group; USA.
Nelson et al., Determinants of DNA Sequence Specificity of the Androgen, Progesterone, and Glucocorticoid Receptors: Evidence for Differential Steroid Receptor Response Elements; Molecular Endocrinology; (1999); vol. 13, No. 12; 2090-2107; The Endocrine Society; Canada.
Onate et al., Sequence and Characterization of a Coactivator for the Steroid Hormone Receptor Superfamily; Science, New Series, (Nov. 24, 1995); vol. 270, No. 5240; 1354-1357; American Assoc. for the Advancement of Science; USA.

(56) References Cited

OTHER PUBLICATIONS

Pierrou et al., Cloning and characterization of seven human forkhead proteins: binding site specificity and DNA bending; The EMBO Journal; (1994); vol. 13, No. 20; 5002-5012; Oxford University Press.
Reddy et al., Genomic determination of the glucocorticoid response reveals unexpected mechanisms of gene regulation; Genome Research; (2009); 2163-2171; Cold Spring Harbor Laboratory Press; USA.
Richer et al., Differential Gene Regulation by the Two Progesterone Receptor Isoforms in Human Breast Cancer Cells; The Journal of Biological Chemistry; (2002); vol. 277, No. 7; 5209-5218; American Society for Biochemistry and Molecular Biology, Inc.; USA.
Roschke et al., Karyotypic Complexity of the NCI-60 Drug-Screening Panel; Cancer Research 63; (Dec. 2003); 8634-8647.
Rossouw et al., Risks and Benefits of Estrogen Plus Progestin in Healthy Postmenopausal Women; JAMA Express; (2002); vol. 288, No. 3; 321-333; American Medical Association; USA.
Scarpin et al., Progesterone action in human tissues: regulation by progesterone receptor (PR) isoform expression, nuclear positioning and coregulator expression; The Open Access Journal of the Nuclear Receptor Signaling Atlas; (2009); vol. 7, e009; 1-13; Australia.
So et al., Determinants of Cell- and Gene-Specific Transcriptional Regulation by the Glucocorticoid Receptor; PLoS Genetics; (Jun. 2007); vol. 3, Issue 6; 0927-0938; USA.
Tang et al., A Comprehensive View of Nuclear Receptor Cancer Cistromes; Cancer Research; (2011 ); 71 (22); 6940-6947; American Association for Cancer Research; USA.
Tseng et al., Progesterone Receptor (hPR) Upregulates the Fibronectin Promoter Activity in Human Decidual Fibroblasts; DNA and Cell Biology; (2003); vol. 22, No. 10; 633-640; Mary Ann Liebert, Inc.; USA.
Vicent et al., Two Chromatin Remodeling Activities Cooperate during Activation of Hormone Responsive Promoters; PLOS Genetics; (2009); vol. 5, Issue 7; 1-13.
Vicent et al., Chromatin Remodeling and Control of Cell Proliferation by Progestins via Cross Talk of Progesterone Receptor with the Estrogen Receptors and Kinase Signaling Pathways; Ann. N.Y. Acad. Sci.; (2006); 1089:59-72; Spain.
Vicent et al., Minireview: Role of Kinases and Chromatin Remodeling in Progesterone Signaling to Chromatin; Molecular Endocrinology; (2010); 1-11; The Endocrine Society; USA.
Vicent et al., Nuclear Factor 1 Synergizes with Progesterone Receptor on the Mouse Mammary Tumor Virus Promoter Wrapped around a Histone H3/H4 Tetramer by Facilitating Access to the Central Hormone-responsive Elements; The Journal of Biological Chemistry; (2010); vol. 285, No. 4; 2622-2631; The American Society for Biochemistry and Molecular Biology, Inc.; USA.
Wang et al., Reprogramming transcription by distinct classes of enhancers functionally defines by eRNA; Nature; (2011); 1-33; Macmillan Publishers Limited.
Wang et al., A Hierarchical Network of Transcription Factors Governs Androgen Receptor-Dependent Prostate Cancer Grow1h; Molecular Cell; (2007); vol. 27; 380-392; Elsevier Inc.
Welboren et al., ChIP-Seq of ERa and RNA polymerase II Defines genes differentially responding to ligands; The EMBO Journal; (2009); vol. 28, No. 10; 1418-1428.
Knutson, et al., Phosphorylated and sumoylation-deficient progesterone receptors drive proliferative gene signatures during breast cancer progession. Breast Cancer Research, 2012, vol. 14: R95.
Metzger E, et al. LSD1 demethylates repressive histone marks to promote androgen-receptor-dependent transcription. Nature (2005) 437: 436-439.
Clarke CL et al., Monoclonal antibodies to human progesterone receptor: characterization by biochemical and immunohistochemical techniques. Endocrinology (1987) 121: 1123-1132.
Graham, JD,et al., Altered progesterone receptor isoform expression remodels progestin responsiveness of breast cancer cells. Mol Endocrinol (2005) 19: 2713-2735.
Guohua et al., Synthesis of Progesterone Receptor Antagonist ZK98299, Zhongguo Yaoke Daxue Xuebao (1992), 23(4), 209-12.

Cantillo (Kappe) et al., A Continuous-Flow Protocol for Light-Induced Benzylic Fluorinations; The Journal of Organic Chemistry, 2014,79,8486-8490.
Schlögl et al, Characteristics of the photochemical prevulcanzation in a falling film protoreactor; Journal of Applied Polymer Science, 2012, 124, 3478.
Puma, et al., Dimensionless analysis of slurry photocatalytic reactors using two-flux and six-flux radiation absorption-scattering models, Catalysis Today, 2007, 122, pp. 78-90.
Kocienski, Carbonyl Protecting Groups, 3rd Edition, Thieme (2005), pp. 58-59.
Neef et al., New Steroids by Simmons-Smith Methyenation and Subsequent Rearrangement, J. Org. Chem., vol. 52, No. 18 (1987), pp. 4143-4146.
Beck, C. A. et al., "Two Types of Anti-progestins Have Distinct Effects on Site-specific Phosphorylation of Human Progesterone Receptor", The Journal of Biological Chemistry (1996) 271: 1209-1217.
Benagiano, G. et al., "Selective progesterone receptor modulators 3: use in oncology, endocrinology and psychiatry", Expert Opin. Pharmacother (2008) 9:2487-2496.
Blankenstein, M. et al., "Occurrence, regulation, and significance of progesterone receptors in human meningiome", Steroids (2000) 65: 795-800.
Bonkhoff, H. et al., "Progesterone Receptor Expression in Human Prostate Cancer: Correlation With Tumor Progression. Prostate" (2001) 48: 285-291.
Bonneterre, J. et al., "Development of a technique to detect the activated form of the progesterone receptor and correlation with clinical and histopathological characteristics of endometrioid adenocarcinoma of the uterine corpus", Gynecologic Oncology (2015) doi: 10.1016/j.ygyno.2015.06.037.
Cameron, S. et al., "Critchley HOD, Buckley CH et al. The effects of post-ovulatory administration of onapristone on the development of a secretory endometrium", Human Reproduction (1996) 11 (1):40-49.
Cameron, S. et al., "Effects of onapristone on postmenopausal endometriurn. Steroids", (2003) 68: 1053-1059.
Cottu, P. et al., "Onapristone (ONA) in progesterone receptor (PR)-expressing tumors: Efficacy and biomarker results of a dose-escalation phase 1 study", J. Clin. Oncol. (2015) 33 (suppl; abstr 5593).
Croxatto, H. et al., "Effect of the antiprogestin onapristone on follicular growth in women", Human Reproduction (1994) 9: 1442-1447.
EP15776251.9 partial supplementary European search report (R 164 EPC) dated Nov. 7, 2017.
Examination Report of Australian Patent Application 2012318618, dated Aug. 9, 2016.
Examination Report of New Zealand Patent Application No. 623140 dated Dec. 8, 2014.
Extended European Search Report of European Patent Application No. 12837954.2 dated Apr. 17, 2015.
Final Office Action dated May 11, 2018 in U.S. Appl. No. 15/378,004.
Goyeneche, A. et al., "Antiprogestins in gynecological diseases" Reproduction (2015) 149: RI5-R33.
Graham, D. et al., "Determination of the activated form of the progesterone receptor (PR) in endometrial cancer (EC)", J. Clin. Oncol. (2013); 3J (suppl; abstr 5602).
Graham, J. "Progesterone receptors—animal models and cell signaling in breast cancer Expression and transcriptonal activity of progesterone receptor A and progestereone receptor B in mamalian cells", Breast Cancer Res (2002) 4: 187-190.
Graham, J. et al., "Expression and transcriptional activity of progesterone receptor A and progesterone receptor B in mammalian cells.", Breast Cancer Research (2002) 4(5):187-190.
Heydarzadeh et al., "Catalyst-free conversion of alkali cellulose to fine carboxymethyl cellulose at mild conditions", (2009) World Appl. Sci. J. 6 (4) 564-569.
Hutt, E. et al., "Clinical and pathological correlation of the activated form of the progesterone receptor (APR) in Endometrial Cancer (EC)", ECC 2013, 1.002.

(56) References Cited

OTHER PUBLICATIONS

International Search Report and Written Opinion dated Feb. 27, 2017 for International Patent Application No. PCT, US2016/066420.
International Search Report of International Patent Application No. PCT/US2012058732 dated Dec. 11, 2012.
International Application No. PCT/US2014/023651, Written Opinion dated Jul. 28, 2014, 11 pgs.
International Preliminary Report on Patentability issued in Internaional Patent Application No. PCT/IB2015/058369 dated May 2, 2017.
International Search Report and Written Opinion for International Patent Application No. PCT/US2017/023256 dated Jun. 16, 2017.
International Search Report issued in International Patent Application No. PCT/IB2015/058369 dated Jan. 25, 2016.
International Search Report of corresponding PCT Application No. PCT/IB 2015/000312 dated Jul. 22, 2015.
International Search Report of PCT Application No. PCT/US2015/060940 dated Jan. 28, 2016.
Ishibashi, H. et al., "Progesterone receptor in non-small cell lung cancer—a potent prognostic factor and possible target for endocrine therapy", Cancer Res. (2005) 65 (14) 6450-8.
John, S. et al. "Chromatin accessibility pre-determines glucocorticoid receptor binding patterns.", (2011) Nat Genet 43: 264-268.
Jonat, W. et al., "Randomized phase 2 study of lonaprisan as second line therapy for progesterone receptor positive breast cancer", Ann Oncol (2013) 24: 2543-2548.
Kim, J. et al., "Progesterone Action in Endometrial Cancer, Endometriosis, Uterine Fibroids, and Breast Cancer", Endocrine Rev. (2013) 34: 130-162.
Koivisto-Korander, R. "Mifepristone as treatment of recurrent progesterone receptor-positive uterine leiomyosarcoma", Obstetrics and Gynecology (2007) 109: 512-514.
Lanari, C. et al., "Antiprogestins in breast cancer treatment: are we ready?", Endocrine-Related Cancer (2012) 19: R35-R50.
Lange, C. et al., "Progesterone Receptor Action: Translating Studies in Breast Cancer Models to Clinical Insights", Innov Endocrinol Cancer (2008) 7: 94-110.
Lasonos, A. et al., "Scientific Review of Phase I Protocols With Novel Dose-Escalation Designs: How Much Information is Needed?", Journal of Clinical Oncology (2015) JCO. 2014.59. 8466.
Meuleman et al., "Morphological and Biochemical Characterization of a Human Liver in a uPA-SCID Mouse Chimera", Hepatology (2005) 41 (4); 847-856.
Mortazavi, A. et al., "Mapping and quantifying mammalian transcriptomes by RNA-Seq.", (2008) Nat Methods 5: 621-628.
Mortel, R. et al., "Heterogeneity and Progesterone—Receptor Distribution in Endometrial Adenocarcinoma", Cancer (1984) 53:113-116.
Mote, P. "Relative expression of progesterone receptors A and B in premalignant and invasive breast lesions", Breast Cancer Research (2000) 2 (Suppl 1) P2.01 doi:1 0.1186/bcrl 03.
Mote, P. et al., "Loss of co-ordinate expression of progesterone receptors A and B is an early event in breast carcinogenesis", Breast Cancer Res Treat (2002) 72(2): 163-72.
Mote, P. et al., "Progesterone receptor isoforms in normal and malignant breast", Ernst Schering Found Symp Proc. (2007) (1):77-107.
Nadji, M. "Immunohistochemistry of Estrogen and Progesterone Receptors Reconsidered: Experience With 5,993 Breast Cancers", Anatomic Pathol. (2005) 123: 21-27.
Neef et al., "New Steroids by Simmons-Smith Methyenation and Subsequent Rearrangement", J_ Org_ Chem., (1987) vol. 52, No. 18 pp. 4143-4146.
Non-Final Office Action dated Mar. 6, 2015 in U.S. Appl. No. 14/205,694.
Notice of Allowance received in U.S. Appl. No. 15/825,697, dated Aug. 9, 2018.
Press, M. et al. "Comparison of different antibodies for detection of progesterone receptor in breast cancer", Steroids (2002) 67:799-813.
Puma, G. L., "Photocatalytic oxidation of multicomponent systems of herbicides: scale-up of laboratory kinetics rate data to plant scale" Catal. Today 2007, 124-132.
Reich, M. et al. (2006) GenePattern 2.0. Nat Genet 38: 500-501.
Rezai et al., "A single-dose PK study of onapristone including the effect of food on absorption", Cancer Chemother. Pharmacol. (2015) 76: 171-177.
Ferland "Synthetic Cardenolides and Related Products. III. Isocardenolides," Canadian Journal of Chemistry (1974) 52,, pp. 1642-1661.
Non-Final Office Action dated Nov. 27, 2018 in U.S. Appl. No. 15/825,697.
Rezai, K. et al., "Population pharmacokinetic (PPK) modeling of onapristone in patients (pts) with progesterone receptor (PR)-expressing cancers", AACR Annual Meeting (2015) Abstract 4523.
Search Report of International Patent Application No. PCT/US2012/058732, dated Dec. 11, 2012.
Search Report of International Patent Application No. PCT/US2015/024792, dated Aug. 7, 2015.
Telleria et al., "Antiprogestins in Ovarian Cancer. Ovarian Cancer—Clinical and Therapeutic Perspectives, DOI: 10.5772/25269", (2012) 207-230.
Written Opinion for PCT/US2017/023256, dated Jun. 16, 2017.
Written Opinion issued in International Patent Application No. PCT/IB2015/058369 dated Jan. 25, 2016.
Written Opinion of International Patent Application No. PCT/US2012/058732, dated Dec. 11, 2012.
Yin, P. et al., "Transcription Factor KLFI 1 Integrates Progesterone Receptor Signaling and Proliferation in Uterine Leiomyoma Cells", Cancer Res. (2010) 70(4); 1722-30.
Zukiwski et al., "Independent characterization by duel staining of progesterone receptor (PR) and estrogen receptor (ER) in breast cancer (BC)", Proc ASCO, abstract No. 118076 (2003).

* cited by examiner

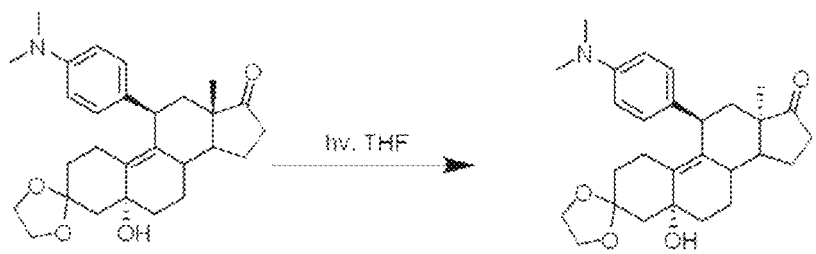

METHODS OF MAKING ONAPRISTONE INTERMEDIATES

PRIORITY CLAIM

This application claims priority to U.S. Provisional Patent Application Ser. No. 62/233,166 filed on Sep. 25, 2015. The above referenced provisional patent application is incorporated herein by reference as if restated in full. All references cited herein, including, but not limited to patents and patent applications, are incorporated by reference in their entirety.

All references cited herein, including but not limited to patents and patent applications, are incorporated by reference in their entirety.

BACKGROUND

Onapristone (ONA) is an anti-progestin drug and progesterone receptor antagonist which was originally developed for contraceptive use. However, it has demonstrated substantial activity in advanced breast cancer. It is thought that ONA binds to the progesterone receptor (PR), preventing the PR from binding to DNA, and thereby inhibits or eliminates PR-induced transcription. See e.g., Klijn et al., Progesterone antagonists and progesterone receptor modulation in the treatment of breast cancer, Steroids, v. 65, pp. 825-830 (2000); Jonat et al., The clinical efficacy of progesterone antagonists in breast cancer, Endocrine Therapy of Breast Cancer, pp. 117-124.

Onapristone is known to be an amorphous compound. For example, (3-Acyloxypropyl)-derivatives of onapristone are crystalline in comparison to the parent compound. Neef, G.; Wiechert, R.; Beier, S.; Elger, W.; Henderson, D. U.S. Pat. No. 4,780,461, 1988. Onapristone has previously been isolated as an amorphous solid and as a yellow oil. Neef, G.; Wiechert, R.; Beier, S.; Elger, W.; Henderson, D. Steroids, 1984, 44, 349; Neef, G Sauer, G.; Wiechert, R.; Beier, S.; Elger, W.; Henderson, D.; Rohde, R. DE3321826, 1984.

U.S. Pat. No. 4,843,157 refers to a process for stereoselection of the desired isomer by photochemical conversion. In this process, photochemical conversion is performed using a "conventional mercury high-pressure lamp" as the radiation source. The preferred wavelengths are identified as ranging from about 250 to about 350 nm. However, the process described in U.S. Pat. No. 4,843,157 (incorporated by reference herein in its entirety) achieved yields in the range of 45 to 60%. Photoconversion of intermediates in the synthesis of progesterone receptor antagonists has also been performed with a mercury lamp at wavelengths of 250-580 nm. See, e.g., Guohua et al., Synthesis of Progesterone Receptor Antagonist ZK98299, Zhongguo Yaoke Daxue Xuebao (1992), 23(4), 209-12.

What is needed is an improved, less costly method for making, forming, or synthesizing onapristone and related compounds with fewer impurities, and fewer and simpler steps.

SUMMARY

In one aspect, methods are described herein for photoconversion of the compound of Formula I:

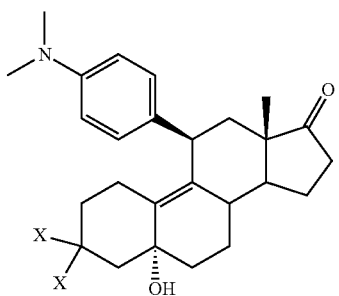

Formula I to the compound of Formula II:

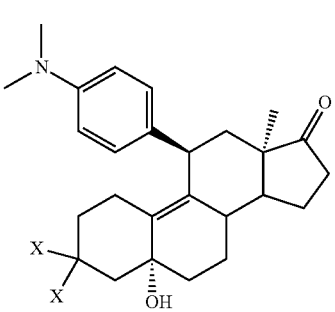

Formula II wherein X is selected from the group consisting of OMe, OEt, OPr, OCH$_2$CH2O and OCH$_2$C(Me)$_2$CH$_2$O.

In one aspect, the compound of Formula I is:

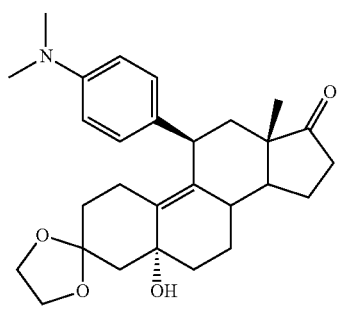 [SMILES: CN(C)c1ccc([C@H]2C[C@]3(C)C(=O)CCC3C3CC[C@@]4(O)CC5(CCC4=C32)OCCO5)cc1]

This compound, (5R,11R,13S)-11-(Dimethylamino)phenyl-5-hydroxy-13-methyl-1,2,5,6,7,8,11,12,13,14,15,16-dodecahydrospiro[cyclopenta[a]phenanthrene-3,2'-[1,3]dioxolan]-17(4H)-one, is also referred to herein as Steroid 1.

In another aspect, the compound of Formula II is:

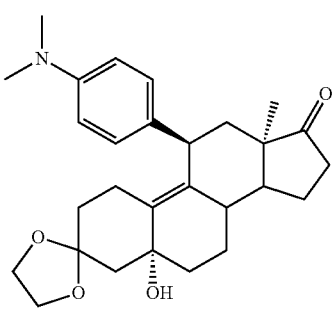 [SMILES: CN(C)c1ccc([C@H]2C[C@@]3(C)C(=O)CCC3C3CC[C@@]4(O)CC5(CCC4=C32)OCCO5)cc1]

This compound, (5-R,11R,13R)-11-(Dimethylamino)phenyl-5-hydroxy-13-methyl-1,2,5,6,7,8,11,12,13,14,15,16-dodecahydrospiro[cyclopenta[a]phenanthrene-3,2'-[1,3]dioxolan]-17(4H)-one), is also referred to herein as Steroid 2.

In one aspect, narrow bandwidth light from a lamp (e.g., excimer Dielectric Barrier Discharge Radiation Source (DBD), (Light-Emitting Diode) LED lamp, OLED (Organic Light-Emitting Diode) lamp, or medium pressure mercury lamp (optionally with filters and at a wavelength of about 280 nm to about 330 nm)) is used to irradiate the compound of Formula I to convert the compound of Formula I to the compound of Formula II (e.g., shifting the C13 methyl group from S to R configuration) resulting in a mixture of Formula I and Formula II with a ratio of about 5-10%:90-95%. In another aspect, the ratio of Formula I to Formula II is about 20:80. In another aspect, the wavelength is from about 300 nm to about 315 nm. In yet another aspect, the wavelength is from about 305 nm to about 310 nm. In another aspect, the wavelength is about 308 nm and the light is emitted from an excimer DBD (dielectric barrier discharge) source.

The resulting mixture can be further purified to increase the percentage of the compound of Formula II (e.g., via functionalization and column chromatography) and used in methods of synthesizing steroids, including onapristone.

FIGURE

FIG. 1 shows an exemplary scheme for photoconversion of the C13 methyl group of the compound of Formula I to the compound of Formula II.

DETAILED DESCRIPTION

Before describing several exemplary aspects described herein, it is to be understood that the invention is not limited to the details of construction or process steps set forth in the following description. The aspects described herein are capable of being practiced or being carried out in various ways.

Aspects described herein provide methods and systems for synthesis of the compound of Formula II through, for example, photoconversion to shift the C13 methyl group from the S to the R position (FIG. 1).

In one aspect, the methods and systems provide a higher yield of the compound of Formula II which increases efficiency and reduces the cost of synthesizing compounds derived from the compound of Formula II, for example, in the synthesis of onapristone.

In another aspect, the compound of Formula I is photo converted into the compound of Formula II through use of narrow band frequency (e.g., about 295 nm to about 320 nm) light generated by, for example, an excimer DBD light source at 308 nm.

In another aspect, the term "photoconversion" refers to the use of light to alter, change, or transform the structure of a chemical compound from one conformation to another conformation (e.g., the position of a substituent on a molecule).

In this aspect, the compound of Formula I is placed in a glass cell which is placed in a photo reactor apparatus. Suitable photo reactors include, but are not limited to, those described in Kappe, O, et al J. Org. Chem, 2014, 79,8486; Schlögl S. et al J. App. Polymer Science, 2012, 124, 3478; and Puma, G. L., Cat. Today, 2007, 124.

In another aspect, the photoreactor can be run in batch or continuous mode. Running the photoreactor in continuous mode could, for example, avoid back mixing or an over reaction.

In another aspect, the photo reactor comprises a glass cell which can contain a solvent and a compound, and a monochromatic light source. In another aspect, photo reactor comprises a quartz glass cell with an 80 um layer gap, one excimer DBD light source (308 nm; power 1*100 W) and optionally a middle pressure mercury lamp with a band filter open between 350 and 410 nm.

In one aspect, the glass cell can be made of quartz, for example. The compound of Formula I can be mixed with a solvent (e.g., THF (tetrahydrofuran), dioxane, MTBE (methyl tertiary butyl ether), diisopropyl ether, diethylether) at a concentration ranging from about 1:10 volumes to about 1:500 volumes.

Alternatively, the photo reactor comprises a plastic tube of suitable diameter wrapped around a (quartz) glass cylinder. In this aspect, irradiation can occur from a light source inserted into the glass cylinder or several light sources placed at suitable distance and angles around the glass cylinder.

In this aspect, exposure of the compound of Formula I to monochromatic light from any suitable lamp converts the C13(R) methyl or alkyl group for a C13(S) methyl or alkyl group forming the compound of Formula II. Suitable lamps include, for example, an excimer radiation source (e.g., emission line 308 nm) available from Heraeus Noblelight. Other suitable lamps include excimer DBD, LED, and others. In another aspect, the lamp emits monochromatic light at a wavelength of about 250 nm to about 350 nm.

Aspects described herein provide methods of making the compound of Formula II

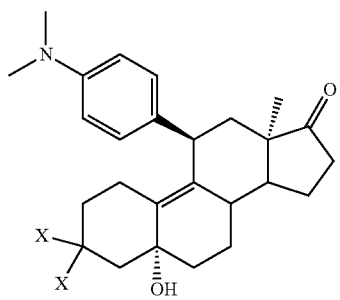

by irradiating the compound of Formula I

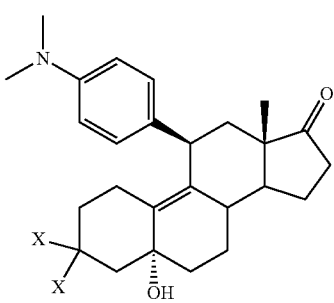

with monochromatic light from a lamp selected from the group consisting of excimer DBD, LED at a wavelength from about 295 nm to about 320 nm. In this aspect, X can be selected from the group consisting of OMe, OEt, OPr, OCH₂CH₂O and OCH₂C(Me)₂CH₂O.

In another aspect, the wavelength of monochromatic light is about 308 nm. In yet another aspect, the lamp is an excimer DBD light source. In another aspect, X is OCH₂CH₂O.

EXAMPLES

The following non-limiting examples illustrate aspects described herein. Not every element described herein is required. Indeed, a person of skill in the art will find numerous additional uses of and variations to the methods described herein, which the inventors intend to be limited only by the claims. All references cited herein are incorporated by reference in their entirety.

Example 1—Photoconversion (5R,11R,13S)-11-(Dimethylamino)phenyl-5-hydroxy-13-methyl-1,2,5,6,7,8,11,12,13,14,15,16-dodecahydrospiro[cyclopenta[a]phenanthrene-3,2'-[1,3]dioxolan]-17(4H)-one (Steroid 1)

A solution of starting material (Formula I) (e.g., 3.5 L containing 200 G starting material 1) is dissolved in 6.5 L THF (tetrahydrofuran) and the solution is transferred into the starting material flask. A cleaned falling film reactor is prepared and the whole system is filled with argon gas. A first cryostat (Cryostat 1) is started at −30° C. A second cryostat Cryostat 2) is started, and the pump set to allow the starting material solution to flow through the falling film reactor to form a steady thin film. Next, an excimer DBD light source set to 308 nm is started, and samples are taken every hour to monitor the reaction progress. The reaction is stopped when little or no starting material can be detected (i.e., when less than 10% of the starting material is detected). After the lamp is turned off, the remaining liquid phase is pumped into the collector flask. The system is washed with THF, and the solution added to the collector flask.

In this aspect, the process of separating the compounds of Formula I and Formula II is simpler than previous methods. Without being bound by theory, it is believed that use of a narrow band light source generates fewer and more polar impurities, which simplifies and reduces the time and cost associated with separating the compounds of Formula I and Formula II.

Although the above description refers to particular aspects, it is to be understood that these aspects are merely illustrative. It will be apparent to those skilled in the art that various modifications and variations can be made to the polymorphic forms and methods described herein. Thus, it is intended that the present description include modifications and variations that are within the scope of the appended claims and their equivalents.

What is claimed is:
1. A method of making the compound of Formula II

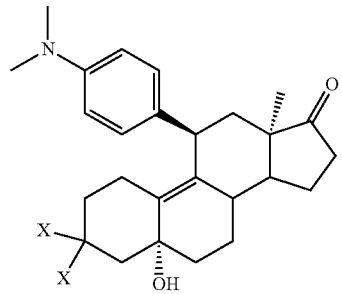

comprising irradiating the compound of Formula I

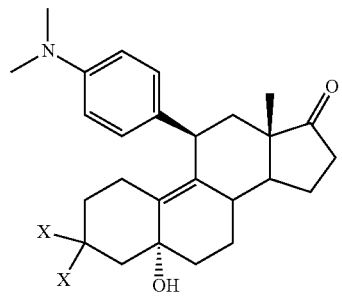

with narrow band frequency light from a lamp selected from the group consisting of excimer DBD light source and LED at a wavelength from about 295 nm to about 320 nm;
wherein taken together the two instances of X combine to form a spirocyclic ring of the formula of —OCH₂CH₂O— or —OCH₂C(Me)₂CH₂O—.
2. The method of claim 1, wherein the wavelength of narrow band frequency light is about 308 nm from a DBD light source.
3. The method of claim 1, wherein the lamp is a DBD light source.
4. The method of claim 1, wherein the ratio of Formula I to Formula II is about 20:80.
5. A method of making Steroid 2:

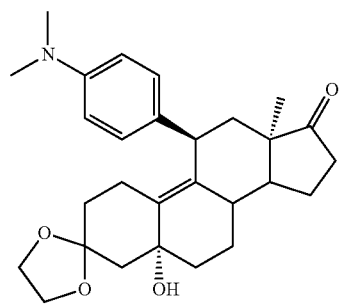 [SMILES: CN(C)c1ccc([C@H]2C[C@@]3(C)C(=O)CCC3C3CC[C@@]4(O)CC5(CCC4=C32)OCCO5)cc1]

comprising irradiating the compound of Formula I

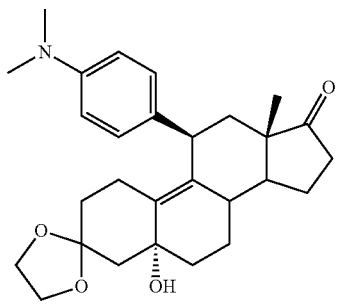 [SMILES: CN(C)c1ccc([C@H]2C[C@]3(C)C(=O)CCC3C3CC[C@@]4(O)CC5(CCC4=C32)OCCO5)cc1]

with narrow band frequency light from a lamp selected from the group consisting of excimer DBD light source and LED, at a wavelength from about 295 nm to about 320 nm.

6. The method of claim 5, wherein the wavelength of narrow band frequency light is about 308 nm.

7. The method of claim 5, wherein the lamp is an excimer lamp.

8. The method of claim 5, wherein the ratio of Formula I to Steroid 2 is about 5-10:90-95%.

9. A method of making the compound of Formula II

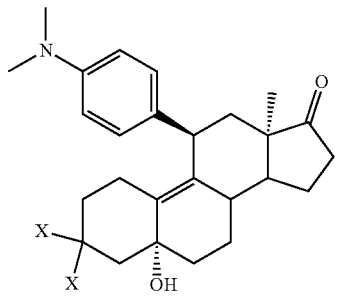

comprising irradiating the compound of Formula I

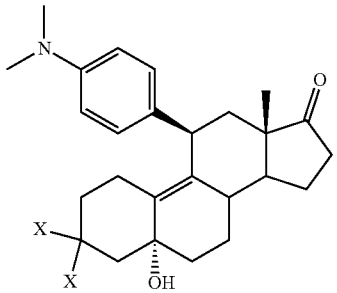

with narrow band frequency light from a lamp selected from the group consisting of excimer DBD light source and LED at a wavelength from about 295 nm to about 320 nm;

wherein X is selected from the group consisting of OMe, OEt, and OPr.

10. The method of claim 9, wherein the wavelength of narrow band frequency light is about 308 nm.

11. The method of claim 9, wherein the lamp is an excimer lamp.

12. The method of claim 9, wherein X is OMe.

13. The method of claim 9, wherein X is OEt.

14. The method of claim 9, wherein X is OPr.

* * * * *